United States Patent [19]

Mendelson

[11] 4,055,573

[45] Oct. 25, 1977

[54] ELECTROCHEMICAL REDUCTION OF IMIDAZOLECARBOXYLIC ESTERS

[75] Inventor: Wilford Lee Mendelson, Philadelphia, Pa.

[73] Assignee: SmithKline Corporation, Philadelphia, Pa.

[21] Appl. No.: 683,863

[22] Filed: May 6, 1976

[51] Int. Cl.$^2$ .................. C07D 233/64; C25B 3/09
[52] U.S. Cl. .................................. 548/335; 204/75
[58] Field of Search .................. 204/72, 73 R, 75; 260/309

[56] References Cited

U.S. PATENT DOCUMENTS

| 815,193 | 3/1906 | Mettler | 204/75 |
|---|---|---|---|
| 815,548 | 3/1906 | Mettler | 204/75 |
| 3,984,293 | 10/1976 | King et al. | 204/75 |

*Primary Examiner*—F.C. Edmundson
*Attorney, Agent, or Firm*—William H. Edgerton

[57] ABSTRACT

Lower alkyl 4-imidazolecarboxylates are electrochemically reduced to give the corresponding alcohol and lower alkyl ethers. This mixture is reacted directly with cysteamine to give the important thioamine intermediates.

10 Claims, No Drawings

ELECTROCHEMICAL REDUCTION OF IMIDAZOLECARBOXYLIC ESTERS

This invention relates to a process for preparing various 4-(hydroxymethyl)-imidazoles and their lower alkyl ethers as well as 4-(2-aminoethylthiomethyl)-imidazoles (thioamines) prepared therefrom.

These compounds are important intermediates for preparing commercially important medicinal agent having histamine $H_2$-antagonist activity of which the inhibition of gastric acid secretion is one medical indication (see Black et al., Nature, 1972, 236-385). An example of one of these end product is cimetidine, N-cyano-N'-methyl-N''-[5-methyl-4-imidazolyl-(methylthio)-ethyl]-guanidine, U.S. Pat. No. 3,950,333.

In a previously filed application, U.S. Ser. No. 602,332, filed Aug. 6, 1975, now U.S. Pat. No. 3,984,293, there is described the state of the art as background to the electrochemical reduction of 4-imidazolecarboxylic acids. That invention is useful, however, it necessitates an extra chemical step prior to reduction, namely hydrolysis of the ester intermediate to form the free carboxylic acid.

There are several review articles on the electrolytic reduction of organic compounds, such as, Popp et al., Chem. Rev., 62; 19-40 (1962) or Eberson, L., Carboxylic Acids and Derivatives, in Baizer, M. M., Organic Electrochemistry; 419 (1973). Other articles are Tafel et al., Chem, Ber.; 37:3187 (1904) or Mettler et al., Chem. Ber.; 37:3692 (1904); 38:1747 (1905); 39:2933 (1906). In summary, none of these references discloses the successful electroreduction of any heterocyclic carboxylic acid. Non-activated aliphatic esters reduce very slowly or not at all while simple aromatic esters, such as benzoates give mixtures of alcohols and ethers, with the latter predominant.

I have now found that electrochemical reduction of lower alkyl 4-imidazolecarboxylates is possible with reaction times often shorter than those used previously for the acid to give a product mix that can be condensed directly with cysteamine to give the desired "thioamine" described above. The term "lower alkyl" is used herein to mean an alkyl group of 1-4 carbon atoms, most usually methyl or ethyl. Propyl or butyl can be alternatively used. The imidazole ring may have various inert substituents, such as 5-lower alkyl especially 5-methyl.

One key to this new process is the discovery that concentrated sulfuric acid, i.e., from about 15% to 50%, especially about 25%, is a superior solvent for the ester starting material whereas the corresponding acid is much less soluble. This enables the electrochemical reaction to be run on concentrated solutions, such as from 1 M. up to the upper limit of solubility (about 30 to 40%). A particularly useful concentration was 1.6 M. (27% W/V) in 25% sulfuric acid. Also most useful are warm solutions of the electrolyte solution, such as from about 40°-75° C., especially about 55°-60° C. The solution may be stirred during the reaction.

Standard electrochemical cell units were used with a voltage of from 3-10 volts. Usually 4-5 volts are applied. Reaction time can be monitored by NMR measurement as described in the Example and typical reaction times are from 10-18 hours. The cathode is typically mercury or preferably lead. The anode is not as critical and may be, for example, platinum or mercury. The catholyte and anolyte are both sulfuric acid. I have found it particularly necessary to clean the surface of the cathode for best results so that contaminants do not poison the surface during reduction. Yields were obtained in the range of from 60-65%. In a reduction using 7.8 g. of ethyl ester in 25% sulfuric acid using a lead electrode I obtained a current efficiency of 25.6% after 18 hours.

I have found moreover that the reduction as described consistently gives two major reduction products, the alcohol and the ether corresponding to the ester starting material. The mixture may comprise as much as 60% alcohol —40% ether or similar ratios neglecting minor amounts of unreacted ester.

The alcohol-ether reaction products can be isolated by neutralizing the electrolyte liquid with any suitable base such as sodium hydroxide and extracting with tert.butyl alcohol.

The reaction mixture as removed from the reduction cell may be used by reacting it directly with a slight excess of cysteamine as the base or salt, such as the hydrochloride or hydrobromide, to give the desired thioamine in 60% yield. The reaction conditions may vary but a typical reaction is conducted at 100°-120° C. with stirring from 3 to 12 hours. The desired thioamine is isolated by methods known to the art as will be evident from the following examples.

EXAMPLE 1

Electrolyte Cell

A cut down 800 ml. beaker with a fitted plastic top. The cathode was made from lead sheet 1/16 inch. The anode was a platinum gauze cylinder, separated from the cathode compartment by a porous clay tube. The catholyte and anolyte were 25% sulfuric acid in "sterile" water.

Power

A 15V, 5A Heath Kit, 1P-2721 power supply.

Activation of Lead Cathode

The cell was assembled and the acid added. A current (−) of 4.5 volts was applied to the lead (as cathode) for five minutes. The lead was removed from the cell, rinsed with distilled water and the surface polished with a plastic soap pad.

The lead was placed in the cell and a current (+) was applied for five minutes. Using the lead as anode, a layer of brown lead oxide forms on its surface. The lead was rinsed with distilled water and polished with a clean plastic soap pad.

The above activation procedure was repeated twice.

Reduction

| Quantities and Assays | |
|---|---|
| 25% Sulfuric Acid | 330 ml. |
| Ethyl 5-methyl-4-imidazolecarboxylate | 80 g. (0.519 M.) |
| Current | 4.75 Amp |
| Voltage | Varied from 4–4.3 volts during this run. |

The fixed current of 4.75 amps was applied to the assembled cell, and the solution stirred magnetically on a hot plate at 50°-55° C. At this time the ester was added over five minutes and the reaction continued for 12 hours. One ml. of the catholyte was placed in an NMR tube and the spectrum was recorded on a standard high resolution NMR spectrometer.

After 18 hours the reduction was stopped and a second set of NMR were recorded. The product was about 50% alcohol and 50% ethylether in 80% yield.

EXAMPLE 2

An "H" type cell was constructed with a coarse sintered disk separating the compartments. The anode was a platinum gauze cylinder, the cathode was a pool of mercury connected by a wire fused in the glass and leading to the power source. For agitation a magnetic stirring bar on the mercury layer was quite efficient. The catholyte and anolyte were 25% sulfuric acid in sterile water.

A solution of ethyl-5-methyl-4-imidazolecarboxylate 6.0 g. (.039 M., 20% W/V) in 30 ml. of 25% sulfuric acid was added to the cathode and stirred at 50° C. An external current of 9 volts was applied and the current stabilized at 1 amp. Potassium dihydrogen phosphate (2.5 g.) was added to increase the conductivity of the solution plus an additional 5 ml. of the 25% sulfuric acid.

After 18 hours, the NMR assay indicated the reduction was 75–85% complete. The reaction was cooled and neutralized to pH 9.5 with ammonia hydroxide. Solid sodium chloride was added and the aqueous solution extracted with four 50 ml. portions of tert.butyl alcohol. The alcohol extractions were washed with saturated sodium chloride and dried with sodium sulfate. After filtration the solution was evaporated to leave 3.8 g. of an oil which was a 55:45 mixture of the ether and the alcohol (76–78% yield).

The ester-alcohol mixture was reacted with cysteamine hydrochloride in acetic acid solution at reflux to give pure thioamine, isolated as the hydrochloride in 60% yield.

EXAMPLE 3

The reaction mixture of 6 g. of ethyl 5-methyl-4-imidazolecarboxylate in 30 ml. of 25% sulfuric acid from either Example 1 or 2 was reacted with cysteamine as follows:

Cysteamine (5.95 g.) was added to the reaction mixture. The solution was warmed slowly to 110°–120° C. bath temperature over two and one-half hours. The mixture was allowed to cool to room temperature, analyzed by TLC then reheated for 3 and one-half hours (reflux temperature 106° C.).

One-half of the cooled reaction mixture was taken to pH 8.7 with 6 ml. of ammonium hydroxide. Salt was added, followed by extraction with four portions of tert.butyl alcohol. The dried extracts were combined and evaporated in vacuo. The resulting oil was slurried in isopropanol then treated with isopropanolic hydrogen chloride. The thioamine product was isolated by cooling the acid mixture to give a white product which was washed with ether and dried in vacuo, 3.49 g., 60%.

EXAMPLE 4

Applying the methods of Examples 1–3 to methyl 4-imidazolecarboxylate gives a mixture of 4-methoxymethylimidazole and 4-hydroxymethylimidazole then the corresponding thioamine.

Applying the method of Examples 1–3 to butyl 5-methyl-4-imidazolecarboxylate gives a mixture of 4-butoxymethylimidazole and 4-hydroxymethylimidazole then the corresponding thioamine.

What is claimed is:

1. The method for preparing a mixture of a 4-(hydroxymethyl)-imidazole and a 4-(lower-alkyloxymethyl)-imidazole which comprises electrochemically reducing in a divided cell a lower alkyl 4-imidazolecarboxylate in 25% sulfuric acid with a mercury or lead cathode at about 40°–75° C. in a concentration chosen from within the range of from 1 M. up to the upper limit of solubility.

2. The method of claim 1 in which the cathode is lead and is maintained free of contaminants.

3. The method of claim 1 in which the lower alkyl is ethyl.

4. The method of claim 1 in which the lower alkyl is methyl.

5. The method of claim 1 in which the lower alkyl is butyl.

6. The method of claim 1 in which the lower alkyl 4-imidazolecarboxylate is ethyl 5-methyl-4-imidazolecarboxylate.

7. The method of preparing 4-(2-aminoethylthiomethyl)-5-methylimidazole comprising electrochemical reduction in a divided cell of a lower alkyl 5-methyl-4-imidazolecarboxylate in 25% sulfuric acid with a mercury or lead cathode at about 40°–75° C. in a concentration chosen from within the range of from 1 M. up to the upper limit of solubility to give a mixture of 5-methyl-4-hydroxymethylimidazole and 5-methyl-4-lower-alkyloxymethylimidazole then reacting said mixture with cysteamine.

8. The method of claim 7 in which the cathode is lead and is maintained free of contaminants.

9. The method of claim 7 in which lower alkyl is ethyl.

10. The method of claim 7 in which said reaction with cyteamine is carried out without isolation of said mixture from the reaction mixture of the reduction.

* * * * *